United States Patent [19]

Pieper

[11] Patent Number: 4,529,559
[45] Date of Patent: Jul. 16, 1985

[54] PROCESS FOR MAKING DERIVATIVES OF VINYLPHOSPHONIC ACID OR VINYLPYROPHOSPHONIC ACID

[75] Inventor: Werner Pieper, Erftstadt, Fed. Rep. of Germany

[73] Assignee: Hoechst Aktiengesellschaft, Fed. Rep. of Germany

[21] Appl. No.: 620,940

[22] Filed: Jun. 15, 1984

[30] Foreign Application Priority Data

Jun. 29, 1983 [DE] Fed. Rep. of Germany ....... 3323392

[51] Int. Cl.$^3$ ............................................. C07F 9/38
[52] U.S. Cl. ............................................. 260/502.4 R
[58] Field of Search ................................. 260/502.4 R

[56] References Cited

U.S. PATENT DOCUMENTS 2,254,124 8/1941 Stevens et al. ............... 260/502.4 R
2,694,684 11/1954 Rogers et al. ................ 260/502.4 R

FOREIGN PATENT DOCUMENTS 0068350 1/1982 European Pat. Off. ...... 260/502.4 R
0899565 1/1982 U.S.S.R. ....................... 260/502.4 R

*Primary Examiner*—J. E. Evans
*Attorney, Agent, or Firm*—Connolly and Hutz

[57] ABSTRACT

The disclosure relates to a process for making derivatives of vinylphosphonic acid or vinylpyrophosphonic acid by reacting a ketone with phosphorus trichloride in the presence of phosphorous acid by using the ketone, phosphorous acid and phosphorus trichloride in a molar ratio of 2:1:1, 1 mol phosphorous acid being replaceable by a further mol phosphorus trichloride and 3 mols water.

8 Claims, No Drawings

PROCESS FOR MAKING DERIVATIVES OF VINYLPHOSPHONIC ACID OR VINYLPYROPHOSPHONIC ACID

The present invention relates to a process for making derivatives of vinylphosphonic acid or vinylpyrophosphonic acid by reacting a ketone with phosphorus trichloride at elevated temperatures.

Vinylphosphonic acid and its derivatives have gained commercial interest as material which can be polymerized to compounds of high molecular weight or processed together with further polymerizable compounds to give a copolymer.

1-phenylvinyl-1-phosphonic acid, its homopolymer and copolymers with other vinyl compounds are used for aftertreating phosphated metal surfaces, for example (cf. German Specification DE-OS No. 24 55 624 and DE-OS No. 26 15 489).

A known process for making substituted vinylphosphonic acids comprises reacting a ketone with phosphorus trichloride in the presence of glacial acetic acid (Houben-Weyl, Methoden der organischen Chemie XII/1, 363-4 (1963). During the reaction, acetyl chloride and hydrogen chloride are split off and presumably cyclic phosphonic acid is obtained which is hydrolyzed to give 1-hydroxyalkane-1-phosphonic acid as an intermediary product which in turn is dehydrated by heating it in an inert solvent, such as 1,1,2,2-tetrachloroethane, to give the desired substituted vinylphosphonic acid (German Patent Specification DE-OS No. 20 60 218).

This process comprising several intermediate stages is very expensive.

We have now unexpectedly found that vinylphosphonic acid derivatives are considerably more easily obtainable by substituting phosphorous acid for glacial acetic acid in the above process.

The process of this invention comprises more particularly: reacting a ketone with phosphorous acid and phosphorus trichloride in a molar ratio of 2:1:1, if desired in an inert solvent, at temperatures between 20° and 150° C., preferably 40°-120° C., 1 mol phosphorous acid being incidentally replaceable by a further mol phosphorus trichloride and 3 mols water so that altogether 1 mol phosphorus trichloride is added to a mixture of ketone and water in the molar ratio of 1:1.5, The ketone should preferably be mixed with the phosphorous acid, the mixture should be heated to reaction temperature and the phosphorus trichloride should be slowly added in metered proportions, resulting hydrogen chloride being allowed to escape.

A preferred feature provides for the ketone to be used in an excess. In this case, the ketone in excess either serves as a reactant and simultaneously as a solvent, or it is used to ensure the formation of a final product containing but little residual phosphorous acid in excess.

A further optional feature of the present process provides for the ketone and phosphorus trichloride to be used in a molar ratio larger than or equal to 1:1, if desired in the inert solvent, and for water, namely for 1.5 mols water, to be added thereto. Needless to say it is possible for 50% of the phosphorus trichloride and for the water to be replaced by the corresponding quantity of phosphorous acid.

In those cases in which a reactive ketone, e.g. acetophenone, is used, it is a vinylpyrophosphonic acid which is predominantly produced and which can be hydrolyzed with the use of stoichiometric quantities of water to give the corresponding vinylphosphonic acid, if desired.

In those cases in which a less reactive ketone is used, the crude product initially obtained is thermally aftertreated, prior to or after hydrolysis. To this end, the reaction product is heated over a period of 1 to 60 minutes to a temperature between the reaction temperature and 250° C. The respective minimum temperature depends on the reactivity of the ketone used. The ketone is selected from compounds of the following general formula

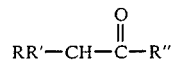

in which R and R' being identical or different each stand for hydrogen or a halogen-substituted or unsubstituted alkyl, aryl, alkaryl or aralkyl group having from 1 to 18 carbon atoms, and R" stands for an alkyl, aryl, alkaryl or aralkyl group having from 1 to 18 carbon atoms.

The process of this invention would not have been expected even by the expert and compares favorably with prior art methods. More particularly, it is no longer necessary to use an auxiliary, such as acetic acid, and the otherwise invariable formation of by-products e.g. acetyl chloride, is avoided. It has already been suggested (German Specification DE-OS No. 31 25 329) that derivatives of vinylphosphonic acid or vinylpyrophosphoric acid should be prepared by reacting a ketone with tetraphosphorus hexoxide in the presence of catalytic amounts of a proton-donating substance, such as $H_3PO_3$, but this process cannot be commercialized. The reason resides in the fact that tetraphosphorus hexoxide is a product which is not commercially available, but has to be made in the laboratory in troublesome and expensive manner and in addition to this is generally contaminated with elemental yellow phosphorus.

The following Examples illustrate the invention which is naturally not limited thereto.

EXAMPLE 1

79.6 g (0.4 mol) p-bromacetophenone and 16.4 g (0.2 mol) phosphorous acid in 100 ml toluene were introduced into a 500 ml multi-necked flask provided with a reflux condenser, thermometer, agitator and dropping funnel and heated to 90°-100° C. Next, 27.5 g (0.2 mol) phosphorus trichloride was added dropwise within 30 minutes with moderate admission of heat. After a post-reaction period of 10 minutes at boiling temperature, the pyro-compound was hydrolyzed by the addition of 3.6 g (0.2 mol) water. After a further post-reaction period of 10 minutes, the whole was allowed to cool. After cooling, 1-(4-bromophenyl)-vinyl-1-phosphonic acid commenced crystallizing out from the solution in the form of colorless needles. 85 g (0.32 mol) phosphonic acid was separated corresponding to a yield of 80.8%. By recycling the mother liquor, it was possible further to improve the yield.

EXAMPLE 2

43.2 g (0.3 mol) α-tetralone and 12.1 g (0.15 mol) phosphorous acid in 90 ml toluene were introduced into an apparatus as described in Example 1 and heated to 90°-120° C. Next, 20.3 g (0.15 mol) phosphorus trichloride was added dropwise, and the whole was then allowed to undergo post-reaction over a period of 30 minutes at boiling temperature. After cooling to 70° C., the whole was hydrolyzed with 2.7 g (0.15 mol) water. After cooling, 56 g (0.27 mol) 3,4-dihydronaphthalene-1-phosphonic acid was separated, corresponding to a yield of 90%. By recycling the mother liquor, it was possible to increase the yield to more than 90%.

EXAMPLE 3

80.4 g (0.67 mol) acetophenone and 27.5 g (0.335 mol) phosphorus acid in 100 ml methylene chloride were introduced into an apparatus as described in Example 1 and heated to boiling. Next, 46.1 g (0.335 mol) phosphorus trichloride was added within 50 minutes. 6.2 g (0.34 mol) water was added, the solvent was distilled off and the residue was heated for 10 minutes to 150° C. 120 g crude product was separated. $^{31}$P-NMR-spectroscopy indicated that it was composed of 91.2 weight % 1-phenylvinyl-1-phosphonic acid, 1.9 weight % 1-hydroxy-1-phenylvinyl-1-phosphonic acid, 5.1 weight % phosphorous acid and 1.8 weight % phosphoric acid.

EXAMPLE 4

184 g (1.53 mols) acetophenone and 41.4 g (2.3 mols) water were introduced into an apparatus as described in Example 1 and heated to 80° C. 210.8 g (1.53 mols) phosphorus trichloride was added dropwise while the temperature was increased to 100° C. towards the end of the dropwise addition. The product was hydrolyzed with 13.9 g (0.77 mol) water and heated for 5 minutes to 150° C. 279 g reaction product was separated. $^{31}$P-NMR-spectroscopy indicated that it was composed of 87% 1-phenylvinyl-1-phosphonic acid and inter alia of 4% phosphorous acid.

EXAMPLE 5

144 g (1.2 mols) acetophenone and 137.5 g (1 mol) phosphorus trichloride were introduced into an apparatus as described in Example 1. The addition of water was started at room temperature. 27 g (1.5 mols) water was added within 35 minutes, the reaction temperature finally reaching 100° C. with gentle supply of heat. Ketone in excess was removed at 150° C. in a water jet vacuum. 141 g crude product was obtained; it was hydrolyzed with 80 ml water and diluted to give 221 g aqueous solution. $^{31}$P-NMR-spectroscopy indicated that the product (based on the anhydrous final product) was composed of about 95 weight % 1-phenylvinyl-1-phosphonic acid and inter alia of about 1.4 weight % phosphoric acid and about 1.2 weight % phosphorous acid.

EXAMPLE 6

49 g (0.5 mol) cyclohexanone and 20.5 g (0.25 mol) phosphorous acid in 100 ml toluene were introduced into an apparatus as described in Example 1 and heated to 90° C. Next, 34 g (0.25 mol) phosphorus trichloride in 50 ml toluene was added dropwise. The solvent was distilled off and the crude product was heated for 2 minutes to 200° C. After cooling to 100° C., the crude product was hydrolyzed with 4.5 g (0.25 mol) water and taken up in glacial acetic acid. 50 g (0.3 mol) cyclohexene-1-phosphonic acid crystallized from the acetic acid solution. This corresponded to a yield of 61.7%.

EXAMPLE 7

300 ml acetone and 27 g (1.5 mols) water were introduced into an apparatus as described in Example 1 and heated to boiling. Next, 137.5 g (1 mol phosphorous trichloride was added dropwise. After a post reaction period of 10 minutes at boiling temperature, the whole was hydrolyzed with 20 ml water; the solvent phase was separated from the resin formed which was subsequently heated for 2 minutes to 200° C. 92 g product was obtained. $^{31}$P-NMR-spectroscopy indicated that the product consisted essentially of 75 weight % propene-2-phosphonic acid and 25 weight % phosphorous acid.

We claim:

1. A process for making a vinyl or substituted vinyl phosphonic or -pyrophosphonic acid from a ketone, comprising:
   reacting the ketone with (a) phosphorus trichloride and (b) phosphorus acid or a partial or total replacement for phosphorus acid, said partial or total replacement for phosphorus acid being the combination of phosphorus trichloride with 3 moles of water for each mole of phosphorus trichloride in said partial or total replacement, the reaction being carried out in an inert solvent in the ketone: (a):(b) molar ratio of 2:1:1.

2. A process according to claim 1, wherein the ketone has the formula:

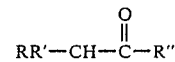

wherein R and R' are identical or different and each stands for hydrogen or a halogen-substituted or unsubstituted alkyl, aryl, alkaryl, or aralkyl group having from 1 to 18 carbon atoms, and R" stands for an alkyl, aryl, alkaryl, or aralkyl group having from 1 to 18 carbon atoms.

3. A process for making vinylphosphonic acids or vinylpyrophosphonic acids by reacting a ketone with phosphorus trichloride at elevated temperatures which comprises: effecting the reaction in the presence of phosphorous acid by using at least two moles of ketone for every mole of phosphorous acid and every mole of phosphorus trichloride, 1 mol phosphorous acid being replaceable by a further mole phosphorus trichloride and 3 mols water.

4. The process as claimed in claim 3, wherein the ketone is mixed with phosphorous acid, the mixture is heated and phosphorus trichloride is metered thereinto.

5. The process as claimed in claim 3, wherein the reaction is carried out in the presence of a solvent.

6. The process as claimed in claim 5, wherein an excess of ketone is used as the solvent.

7. The process as claimed in claim 5, wherein the solvent is inert toward the reactants.

8. The process as claimed in claim 3, wherein the reaction is carried out at temperatures between 20° and 150° C.

* * * * *